United States Patent [19]

Totani et al.

[11] Patent Number: 5,011,602
[45] Date of Patent: Apr. 30, 1991

[54] ANTIBACTERIAL MATERIAL FOR WATER

[75] Inventors: Tuyoshi Totani, Tokyo; Tatuo Yamamoto, Inazawa; Yasuo Kurihara, Nagoya, all of Japan

[73] Assignee: Shinagawanenryo Kabushikikaisha, Tokyo, Japan

[21] Appl. No.: 362,538

[22] Filed: Jun. 7, 1989

[30] Foreign Application Priority Data

Jun. 16, 1988 [JP] Japan ................... 63-149195

[51] Int. Cl.⁵ ................................................. C02F 1/50
[52] U.S. Cl. ................................. 210/484; 210/242.1; 210/501
[58] Field of Search ................. 210/242.1, 484, 501

[56] References Cited

U.S. PATENT DOCUMENTS

| | | | |
|---|---|---|---|
| 964,696 | 7/1910 | Roche | 210/242.1 |
| 4,016,080 | 4/1977 | Williams | 210/501 |
| 4,396,512 | 8/1983 | Beauman et al. | 210/501 |
| 4,608,247 | 8/1986 | Heinig | 210/501 |

FOREIGN PATENT DOCUMENTS 60-181002 9/1985 Japan.

Primary Examiner—Ivars Cintins
Attorney, Agent, or Firm—Pollock, Vande Sande & Priddy

[57] ABSTRACT

An antibacterial material for water comprising a carrier containing an antibacterial agent and a fabric surrounding it is disclosed. When this antibacterial material for water is placed in water, microorganisms living in the water would pass through the fabric and approach the carrier, so that they are attacked by the antibacterial agent contained therein and die. On the other hand, contaminants and slime in the water cannot approach the carrier since they are filtered off by the fabric. Therefore the surface of the carrier is hardly coated with contaminants or slime and kept in an exposed state. As a result, the antibiotic effect of the antibacterial material on the water can be maintained for a long period of time.

4 Claims, 1 Drawing Sheet

000
ANTIBACTERIAL MATERIAL FOR WATER

BACKGROUND OF THE INVENTION

1. Field of the Invention

This invention relates to an antibacterial material for water which is used to sterilize water to thereby inhibit the propagation of microorganisms therein.

2. Description of the Prior Art

A known antibacterial material for water comprises a particulate antibacterial composition comprising zeolite as a carrier, wherein metal(s) capable of ion exchange contained in said zeolite are exchanged with at least one metal selected from among silver, copper and zinc (cf. Japanese Patent Laid-Open No. 181002/1985).

When the abovementioned antibacterial material is placed in water, the antibacterial agent such as silver, copper or zinc contained in said antibacterial material would attack microorganisms living in the water to thereby kill them.

When the antibacterial material is kept in water for a prolonged period of time, however, the surface of the antibacterial material might be coated with, for example, contaminants in the water and slime, so that the microorganisms living in the water would never be attacked by said antibacterial agent contained in the antibacterial material any more. Namely, the antibacterial material can no longer exert its antibiotic effect.

SUMMARY OF THE INVENTION

It is an object of the present invention to provide an antibacterial material for water which can kill microorganisms living in water when placed therein.

The antibacterial material of the present invention comprises a carrier containing an antibacterial agent and a fabric surrounding said carrier which involves as small voids as possible among a number of fibers so long as water and microorganisms therein can pass therethrough.

When this antibacterial material for water is placed in water, microorganisms living in the water pass through the fabric together with the water as the water moves. After passing through the fabric, these microorganisms approach the carrier. Thus they are attacked by the antibacterial agent contained in said carrier and die.

It is another object of the present invention to provide an antibacterial material for water capable of killing microorganisms living in water at the same efficiency when retained in water for a prolonged period of time, i.e., an antibacterial material for water showing a sustained antibiotic effect.

When the abovementioned antibacterial material for water of the present invention is placed in water, the water and microorganisms living therein can pass through the fabric while contaminants in the water and slime are filtered by said fabric surrounding said carrier and thus prevented from approaching the carrier. Therefore the surface of the carrier is hardly coated with contaminants or slime but kept in an exposed state. In this case, the contaminants or slime might adhere to the surface of said fabric. Since, however the surface of the fabric is highly uneven, the contaminants and slime adhering thereto, if any, take an extremely long period of time to cause complete jamming of the fabric. Accordingly the water and microorganisms can pass through the fabric for a long time and the antibiotic effect of the antibacterial material of the present invention on water can be maintained during this period.

DESCRIPTION OF THE PREFERRED EMBODIMENTS

Figure 1:
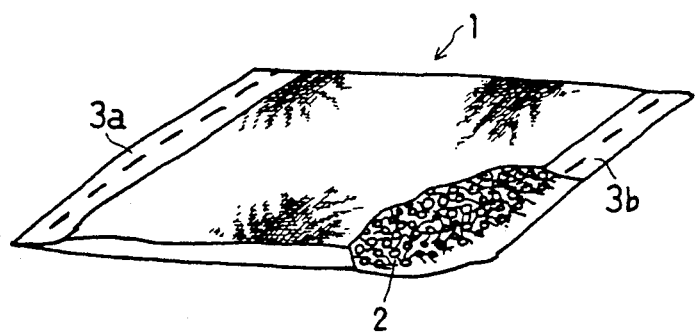
FIG. 1 is a partial sectional view of the antibacterial material for water of the present invention.
Figure 2:
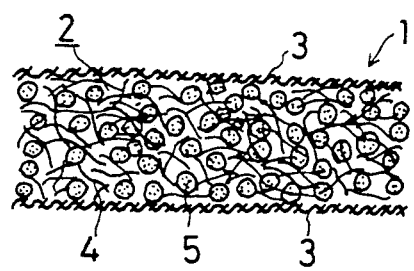
FIG. 2 is an enlarged sectional view of the same.

Now FIGS. 1 and 2, each showing an example of the antibacterial material for water of the present invention, will be described in detail. An antibacterial material 1 for water is formed into a sheet which comprises a pulp paper product 2 containing an antibacterial agent and a fabric 3 surrounding said pulp paper product 2. The fabric 3 is in the form of a bag whose ends 3a and 3b are sealed to thereby enclose said pulp paper product 2 therein. The pulp paper product 2 is prepared by mixing a carrier containing the antibacterial agent with pulp and treating the obtained mixture with a paper machine. In FIG. 2, 4 represents the pulp while 5 represents the carrier containing the antibacterial agent. Said carrier containing the antibacterial agent is one which carries the antibacterial agent by, for example, adsorption, binding or ion exchange.

Said fabric 3 is employed in order to filter off the contaminants which may cause the formation of slime such as dead microorganisms upon passage of the water and microorganisms living therein through the fabric. It is preferable, therefore, that the fabric includes voids as small as possible among a number of fibers, so long as the water and microorganisms living therein can pass therethrough. The upper limit of the void size of said fabric may be determined in such a manner as not to inhibit the filtration of the contaminants and slime in the water.

This antibacterial material 1 for water is thrown into water to be sterilized, namely, placed in the bottom of the water or suspended therein. Then the water and microorganisms, such as bacteria and fungi, living therein pass through said fabric 3 as the water moves. After passing through the fabric 3, these microorganisms approach said carrier 5. Then they are attacked by said antibacterial agent contained therein and die. In the case of flowing water, the abovementioned movement of the water may be caused as the water flows. In the case of retained water, on the other hand, it may be caused by the convection of the water, the movement of water molecules, or the like.

When the antibacterial material for water is placed in water, as described above, the water is filtered by the fabric 3 and thus the contaminants and slime in the water cannot approach the carrier 5. Therefore the surface of the carrier 5 containing the antibacterial agent is prevented from being is coated with the contaminants or slime. Even if the filtered contaminants or slime adhere to the surface of the fabric 3, it takes an extremely long period of time for them to completely coat the surface of the fabric 3, since the latter has a highly uneven surface and a large surface area. These facts suggest that the antibacterial material 1 for water can exert the abovementioned antibiotic effect for a prolonged period of time.

In addition, the fabric 3 suppresses the leakage of the carrier 5 or the antibacterial agent contained therein outside the fabric 3, when the antibacterial material is used in the abovementioned manner. Thus the sustained antibiotic effect of the antibacterial material is further elevated thereby.

Now the antibacterial material for water of the present invention will be described in more detail.

Examples of the abovementioned antibacterial agent include ions and compounds of metals such as silver, copper, zinc, mercury, lead, tin, bismuth, cadmium and thallium. Further halogen compounds such as stabilized chlorine, hypochlorites, chloramine and ethylene iodide may be used therefor. Furthermore, organic compounds such as alcohols, phenols, ethers, guanidines, thiazoles, quaternary ammonium salts, thiocarbamates and surfactants may be used therefor. Among these compounds, silver, copper and zinc ions and compounds thereof are preferable as the antibacterial agent to be used in the present invention, since they have a high antibacterial effect and are yet harmless to the human being.

The abovementioned carrier carries said antibacterial agent through, for example, adsorption, binding or ion exchange. This carrier is employed in order to make sure that the antibacterial agent is neither dissolved in water nor decomposed but can exert a stable antibacterial effect. Examples of the carrier include silica gel, alumina, synthetic or natural crystalline aluminosilicate, amorphous aluminosilicate, activated clay, sepiolite, clayey material and active carbon. Among these materials, an amorphous aluminosilicate, which will be referred to as AAS hereinafter, is preferable as the carrier to be used in the present invention, since it is porous and has a large specific surface area and thus can carry a large amount of the antibacterial agent.

As the carrier containing said antibacterial agent, an amorphous aluminosilicate wherein part or the whole of ions capable of ion exchange are substituted with the abovementioned antibacterial metal ions may be used. In this case, conventional AAS may be used without any restriction. AAS is generally represented by the formula:

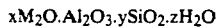

$$xM_2O \cdot Al_2O_3 \cdot ySiO_2 \cdot zH_2O$$

wherein M generally represents an alkali metal element such as sodium or potassium; and x, y and z represent the molar ratios of a metal oxide, silica and water of crystallization, respectively.

When silver is to be used among the abovementioned antibacterial metals, it may be appropriately added in an amount of 0.1 to 50%, preferably 0.5 to 5%, in order to achieve an excellent antibacterial effect. It is further preferable that silver is used together with 0.1 to 15% of at least one metal selected from among copper, zinc, mercury, tin, lead, bismuth, cadmium, chromium and thallium.

The abovementioned antibacterial AAS may be prepared by, for example, the following process (1) or (2).

(1) Amorphous aluminosilicate preferably containing not more than 10% of $M_2O$, wherein M represents an alkali metal, is contacted with antibacterial metal ions. Thus the ions capable of ion exchange which are present in the amorphous aluminosilicate is substituted with the antibacterial metal ions to thereby give the aimed antibacterial AAS.

(2) The pH value of an amorphous aluminosilicate slurry is adjusted to, preferably, 6 or below. Then the amorphous aluminosilicate in said slurry is contacted with antibacterial metal ions. Thus the ions capable of ion exchange are substituted with the antibacterial metal ions to thereby give the aimed antibacterial AAS.

The amorphous aluminosilicate (AAS) to be used in the process (1) preferably contains not more than 10% of $M_2O$. AAS obtained by a common method contains more than 10% of $M_2O$. Thus the AAS obtained by the common method is suspended in, for example, water. To the slurry thus obtained is added dropwise an aqueous acid solution under stirring. Thus the alkali metal(s) and/or alkaline earth metal(s) present in the AAS are neutralized and the $M_2O$ content in the AAS, can be lowered to 10% or less thereby. A dilute aqueous acid solution of a concentration of 0.1 N or below may be used as the aqueous acid solution. The addition may be preferably conducted at a rate of 100 ml/min or below, though it may vary depending on the stirring conditions and the reaction scale. It is further preferable that the neutralization is conducted to make the pH value of the slurry to 3 to 6, still preferably 4 to 5. Examples of the acid to be used in the neutralization include inorganic acids such as nitric acid, sulfuric acid, perchloric acid, phosphoric acid and hydrochloric acid and organic acids such as formic acid, acetic acid, oxalic acid and citric acid.

The AAS containing not more than 10% of $M_2O$ thus obtained is then filtered and washed with water. Then the resulting slurry may be subjected to the process (1) as such. Alternately, the slurry may be dried to thereby give AAS of an $M_2O$ content of 10% or below. In the process (1), it is preferable to mix an AAS slurry containing 10% or less of $M_2O$ with an aqueous solution containing the antibacterial metal ions. Thus the AAS is contacted with the aqueous solution containing a mixture of antibacterial metal ions such as silver, copper and/or zinc ions. As a result, the ions capable of ion exchange contained in the AAS are substituted with the abovementioned metal ions. The contact may be conducted at 5° to 70° C., preferably 40° to 60° C., for 1 to 24 hours, preferably 10 to 24 hours. It may be carried out either batchwise or continuously by using, for example, a column.

Each ion in the abovementioned aqueous solution may be supplied in the form of a salt. For example, silver ions may be supplied as diammine silver nitrate or diammine silver sulfate; copper ions may be supplied in the form of copper (II) nitrate, copper perchlorate, copper acetate, potassium tetracyanocuprate or copper sulfate; zinc ions may be supplied in the form of zinc (II) nitrate, zinc sulfate, zinc perchloriate, zinc thiocyanate or zinc acetate; mercury ions may be supplied in the form of mercury perchlorate or mercury acetate; tin ions may be supplied in the form of tin sulfate; lead ions may be supplied in the form of lead sulfate or lead nitrate; bismuth ions may be supplied in the form of bismuth chloride or bismuth iodide; cadmium ions may be supplied in the form of cadmium perchlorate, cadmium sulfate, cadmium nitrate or cadmium acetate; chromium ions may be supplied in the form of chromium perchlorate, ammonium chromium sulfate or chromium acetate; and thallium ions may be supplied in the form of thallium perchlorate, thallium sulfate, thallium nitrate or thallium acetate.

The content of, for example, the silver ions in the AAS may be appropriately controlled by adjusting the concentration of each ion (salt) in the abovementioned mixed aqueous solution. When the antibacterial AAS contains silver ions, for example, the silver ion content of the antibacterial AAS may be adjusted to 0.5 to 6% by controlling the silver ion concentration of the abovementioned mixed aqueous solution within a range of 0.01 to 0.30 M/l. When the antibacterial AAS further contains copper and zinc ions, the content of these ions of said antibacterial AAS may be adjusted to 1 to 10% and 1 to 12%, respectively, by controlling the copper ion and zinc ion concentrations of the abovementioned mixed aqueous solution each within a range of 0.05 to 3.0 M/l.

Alternately, the AAS may be successively contacted with aqueous solutions each containing one of the abovementioned metal ions alone, instead of with the abovementioned mixed aqueous solution, to thereby effect the ion exchange. The concentration of the metal ion in each aqueous solution may be determined in a similar manner as those described in the case of the above mixed aqueous solution.

Further an ammonium ion or an ion of an amine, such as methylamine, may be added to the mixed aqueous solution in conducting the ion exchange to thereby stabilize the silver, copper and/or zinc ions.

After the completion of the ion exchange, the AAS is thoroughly washed with water and dried the drying may be preferably conducted at 105° to 115° C. under an atmospheric pressure or under a reduced pressure (1 to 30 Torr).

In the case of ions which cannot form any appropriate water-soluble salts, such as tin or bismuth, or organic ions, the ion exchange may be carried out by using an organic solvent such as an alcohol or acetone to thereby prevent the precipitation of hardly soluble basic salt(s).

In the process (2), on the other hand, the pH value of the AAS slurry obtained in a conventional manner may be adjusted to 6 or below, preferably 3 to 6 and still preferably 4 to 5, to thereby control the $M_2O$ content of the AAS to 10% or below. The pH value may be adjusted in the same manner as the one described in the above process (1).

Then the slurry, with its pH value adjusted as described above is mixed with a solution containing antibacterial metal ions to thereby carry out the ion exchange of AAS. The ion exchange may be conducted in the same manner as the one described in the above process (1).

The abovementioned inorganic carrier has a specific surface area of 500 $m^2/g$ or above, preferably 700 $m^2/g$ or above.

The carrier containing the abovementioned antibacterial agent may be used in various forms optionally together with other materials. Namely, it may be formed into, for example, powders, pellets, spheres, granules, foaming products or hollowing products alone. Alternately, it may be mixed with, for example, pulp or resins to thereby give pulp paper products or molded resin products, respectively.

Pulp paper products and molded resin products are preferable, since they would be hardly deformed or crushed into particles.

The oozing of the antibacterial agent can be reduced by providing a filtering fabric around the carrier containing said antibacterial agent. Said fabric is further effective in preventing dead microbial cells from directly adhereing to the surface of the antibacterial material. Thus the antibacterial material can exert a stabilized antibiotic effect for a prolonged period of time. Any material may be used as the filtering fabric, so long as it can reduce the oozing of the antibacterial agent or the carrier containing the same to a level of 0.1 ppm or below. Preferable examples thereof include woven fabrics made of natural or synthetic fibers, knitted webs, nonwoven fabrics and warifus. It is widely known that these fabrics, knitted webs and nonwoven fabrics are each a sheet-like material consisting of a number of fibers. Thus these materials inherently involve a number of fine voids through which water can permeate, which brings about the desired filtering effect.

In contrast thereto, water can never permeate through a nonporous sheet. However such a nonporous sheet becomes available as the filtering fabric to be used in the present invention by perforating the same to thereby artificially form a number of pores and then stretching the perforated sheet in one direction in such a manner as to have smaller pores. The sheet material thus obtained is called a "warifu". Among these materials, nonwoven fabrics are particularly preferable from the viewpoints of filtration capability, air-permeability and processability.

A nonwoven fabric is a fabric material having a web or mat-like structure consisting of fibers which are bound to each other via an adhesive.

A nonwoven fabric may be produced either by a wet process or a dry one. The former process comprises molding relatively short fibers by using water as a medium in such a manner as the one used in paper making and then drying the molded product. The dry process comprises adhereing fibers by an adhesive to thereby mold the same; mechanically binding fibers with, for example, a needle punch; or simultaneously spinning and molding fibers, i.e., a spun-bond method. Each of these procedures may be employed in the preparation of the nonwoven fabric to be used in the present invention. The nonwoven fabric may be made of, for example, rayon, vinylon, a polyamide resin, an acryl resin, a polyester resin, a polypropylene resin, a polyethylene resin, an acetate resin, a vinyl chloride resin, polyclar resin, cotton, linen, cocoons or cotton linter. The nonwoven fabric may comprise one or more materials selected from among rayon, a polyester resin, a polypropylene resin and a polyamide resin from the viewpoints of water-permeability, moisture retention, mechanical strengths and heat-sealability.

The abovementioned nonwoven fabric preferably has a metsuke ranging from 10 to 180 $g/m^2$. The term "metsuke" used herein represents the mesh size, i.e. the basis weight of a nonwoven fabric and is expressed in the weight per square meter ($g/m^2$). A nonwoven fabric of a metsuke of 10 $g/m^2$ or below is excessively thin and a large amount of contaminants and slime in water would pass therethrough and enter the inside. Furthermore a large amount of the antibacterial agent enclosed in the fabric may leak therefrom in this case. On the other hand, a nonwoven fabric of a basis weight of 180 $g/m^2$ or above is too thick and thus has a poor water permeability. Namely, water in the outside of the fabric and microorganisms in the water can hardly enter the inside of the fabric. Thus no satisfactory antibiotic effect can be achieved in this case.

It is preferable that the nonwoven fabric has a thickness of 0.1 to 1.8 mm. The surface of a nonwoven fabric of a thickness of less than 0.1 mm is scarcely uneven. Thus even a small amount of contaminants and slime adhering thereto might cause jamming, which makes the permeation of water and microorganisms living therein difficult. Further a large amount of the antibacterial agent would leak from the inside to the outside of the fabric in this case. On the other hand, a nonwoven fabric having a thickness exceeding 1.8 mm has a poor water-permeability.

We have examined the oozing of silver, which was one of the antibacterial agents, and waterpermeabilities of nonwoven fabrics of various basis weight and thicknesses. Table 1 summarizes the results. Polyester spunbond nonwoven fabrics were employed in this test. A carrier enclosed in each nonwoven fabric was a pulp paper product comprising the antibacterial aluminosilicate sample No. 5 as will be shown in Table 2 hereinafter.

TABLE 1

| Basis Weight (g/m$^2$) | Thickness (mm) | Silver oozing (ppb) | Water-permeability (cc/cm$^2$/sec) |
| --- | --- | --- | --- |
| 10 | 0.1 | 78 | 125 |
| 20 | 0.2 | 38 | 88 |
| 50 | 0.5 | 21 | 72 |
| 100 | 0.9 | 16 | 58 |
| 150 | 1.5 | 6 | 41 |
| 180 | 1.8 | 2 or less | 15 |
| 250 | 2.2 | 2 or less | 2 |

Note: Preferable silver oozing is 50 ppb or below.

The fabric may be provided around the carrier containing the antibacterial agent by a number of commonly employed methods. For example, the carrier is enclosed in a fabric bag by heat sealing. Alternately, the carrier is put into a cylindrical container and then the filtering fabric is provided at both ends of the cylinder.

When the abovementioned antibacterial material for water is to be used in the sterilization of water, the carrier containing the antibacterial agent is preferably used in an amount of 0.005 to 5%, still preferably 0.01 to 0.5%, based on the water or a water-containing solution to be sterilized in order to achieve a sustained antibiotic effect, regardless of the fabric material.

The antibacterial material for water of the present invention shows high antibacterial and/or antifungal effects. It is further effective in the inhibition of the growth of algae. Thus this antibacterial material for water is widely available in treating, for example, tap water, industrial water and sewage; in the sterilization of water retained in, for example, a drinking water cooler, a cooling tower, a pool, a moistener, a cold air fan, a toilet water tank, a water tank of an electric steam stove, a contact lens case, a straining basket, bath tub and lavatory traps (S-tubes), an underground rainwater tank of a building or an elevated water tank; and in the sterilization of aqueous emulsions such as a metal processing oil or a water-base coating, though the applications thereof are not restricted thereby.

Now Examples of a process for the production of the antibacterial material for water of the present invention and the results of various examinations on the antibacterial material for water thus obtained will be given.

REFERENTIAL EXAMPLE 1: PREPARATION OF AAS 19.4 kg of aluminum hydroxide was added to 22.3 kg of a 49% solution of sodium hydroxide and dissolved therein under heating. Then 34.7 l of water was added thereto and the obtained mixture was maintained at 30° C. (solution I).

Separately, 25.5 l of water was added to 42.0 kg of sodium silicate and the mixture was maintained at 30° C. (solution II). These solutions I and II were added to a reaction tank containing a solution prepared by adding 21.3 l of water to 4.1 kg of a 49% solution of sodium hydroxide (solution III). Subsequently the resulting mixture was allowed to react at 50±2° C. under stirring for 30 minutes. The product thus formed was filtered and the solid matters were washed with warm water to thereby remove the excessive alkali. After drying at 100° C., a sample of AAS was obtained. The chemical composition ratio of this sample was as follows:

$Na_2O: Al_2O_3: SiO_2 = 0.93:1:2.55$.

It showed no diffraction peak in X-ray diffractometry, which indicated that it was amorphous aluminosilicate.

REFERENTIAL EXAMPLE 2: PREPARATION OF ANTIBACTERIAL ALUMINOSILICATE

Three aluminosilicates, namely, commercially available type A zeolite ($Na_2O.Al_2O_3. 1.9 SiO_2.XH_2O$; mean particle size: 1.5 μm), commercially available type Y zeolite ($1.1 Na_2O.Al_2O_3.4.1 SiO_2.XH_2O$, mean particle size: 0.7 μm) and the amorphous aluminosilicate obtained in the above Referential Example 1 ($0.93 Na_2O.Al_2O_3.2.55 SiO_2.XH_2O$, mean particle size: 0.3 μm) were employed. Further five salts including $NH_4NO_3$, $AgNO_3$, $Cu(NO_3)_2$, $Zn(NO_3)_2$ and methylamine were used as salts providing ions for ion exchange. Table 2 shows the aluminosilicate, the salts contained in the mixed aqueous solution and the concentrations thereof which were used in the preparation of each antibacterial aluminosilicate sample. Under these conditions, nine antibacterial aluminosilicate samples No. 1 to No. 9 shown in Table 2 were obtained.

Each sample was obtained in the following manner. Namely, water was added to 1 kg of an aluminosilicate powder, which had been dried at 110° C., to thereby give 1.3 l of a slurry. The slurry was then degassed by stirring. Further an appropriate amount of a 0.5 N solution of nitric acid and water were added thereto and the pH value of the slurry was adjusted to 5 to 7. Thus the total volume of the slurry was adjusted to 1.8 l. Then 3 l of the aqueous solution of mixed salts of given concentrations, which was employed for ion exchange, was added thereto to thereby give a total volume of 4.8 l. This slurry was kept in an equilibrated state under stirring while maintaining at 40° to 60° C. for 10 to 48 hours. After the completion of the ion exchange, the aluminosilicate phase was filtered and washed with cold or warm water until it contained no excessive silver, copper and/or zinc ions. Subsequently the obtained sample was dried at 110° C. Thus the nine samples were obtained. Table 2 shows the data relating to the antibacterial aluminosilicate samples Nos. 1 to 9 thus prepared.

PRODUCTION EXAMPLE 1 OF ANTIBACTERIAL MATERIAL FOR WATER (PRODUCTION OF ANTIBACTERIAL SHEET)

0.8 kg of ground pulp was thoroughly mixed with 3.2 kg of an antibacterial agent-containing carrier obtained in Referential Example 2. The dispersion thus obtained was treated with a paper machine at a rate of one sheet per five minutes to thereby give a sheet (600×600×1 mm). The obtained paper product was then cut into pieces of 100×100×1 mm in size and put into a nonwoven fabric bag (120×120 mm). The bag was then sealed with a heat sealer at 220° to 230° C. Thus seven samples A to G of antibacterial material for water, each in the form of a sheet, were obtained (cf. Table 3).

ANTIBIOTIC EFFECT TEST

A sheet of each of the Samples A to G of the antibacterial material for water obtained in the above Production Example 1 and a 4 g portion of each of the Samples Nos. 1 and 5 of the antibacterial aluminosilicate powder prepared in Referential Example 2 were each put into a solution prepared by adding 100 ml of a $10^5$/ml solution of *Staphylococcus aureus* to 5.9 l of pure water and another solution prepared by adding 100 ml of a $10^5$/ml solution of *Pseudomonas aeruqinosa* to 5.9 l of pure water and allowed to stand therein at 20° to 23° C. for 30 days. During this period, the change in the bacterial count per ml of each solution was monitored to thereby evaluate the antibiotic effect of each sample. The results are shown in Table 4 (Test Nos. 1 to 9). For comparison, the change in the bacterial count of a solution prepared by adding each bacterial solution to pure water was also monitored. The results are shown in Table 4 (Test No. 10).

OOZING TEST

Each of the Samples A to G of the antibacterial material for water obtained in Production Example 1 and each of the Samples Nos. 2, 7 and 8 of the antibacterial aluminosilicate powder obtained in Referential Example 2 were put into 5.9 l of pure water and stirred with a stirrer at 50 rpm for ten hours. The silver which had oozed in the supernatant was determined by atomic absorption spectrometry and the oozing of the antibacterial metal was evaluated thereby. The results are shown in Table 5 (Test Nos. 1 to 10).

For comparison, 4 g of silver-spreaded active carbon involved in a commercially available water treatment system (granules, silver content: 0.08 g/4 g) was treated in the same manner to thereby evaluate the oozing of the silver. The results are shown in Table 5 (Test No. 11).

TABLE 2

| Sample No. | Alumino-silicate | Content in aluminosilicate (%) | | | | | Ion exchange solution (M/l) | | | | | Yield (g) | Ion exchange time (Hr) | Specific surface area (m²/g) |
|---|---|---|---|---|---|---|---|---|---|---|---|---|---|---|
| | | $NH_4$ | Ag | Cu | Zn | Methylamine | $NH_4NO_3$ | $AgNO_3$ | $Cu(NO_3)_2$ | $Zn(NO_3)_2$ | Methylamine | | | |
| 1 | type A zeolite | 0.9 | 2.1 | | 12.1 | | 0.60 | 0.07 | | 3.0 | | 960 | 15 | 720 |
| 2 | type A zeolite | 1.2 | 2.6 | | | | 0.85 | 0.07 | | | | 910 | 15 | 720 |
| 3 | type Y zeolite | | 1.5 | 8.6 | | | | 0.05 | 2.0 | | | 940 | 48 | 930 |
| 4 | type Y zeolite | | 0.8 | | 6.3 | 0.5 | | 0.04 | | 1.0 | 0.80 | 960 | 30 | 930 |
| 5 | AAS | 0.5 | 0.5 | | 10.3 | | 0.50 | 0.03 | | 2.5 | | 960 | 24 | 860 |
| 6 | " | 2.2 | 1.8 | 6.2 | | | 1.40 | 0.06 | 1.8 | | | 950 | 24 | 860 |
| 7 | " | | 2.6 | | | 0.8 | | 0.07 | | | 1.00 | 960 | 20 | 860 |
| 8 | " | 1.8 | 2.6 | | | | 1.60 | 0.07 | | | | 960 | 20 | 580 |
| 9 | " | | 2.0 | | 6.3 | | | 0.06 | | 1.0 | | 970 | 20 | 580 |

TABLE 3

| Sample No. | Antibacterial aluminosilicate No. | Nonwoven fabric (manufacturer) | | | Content (g/sheet) | | |
|---|---|---|---|---|---|---|---|
| | | Type | Basis Weight (g/m²) | Thickness (mm) | Silver | Copper | Zinc |
| A | 1 | Nylon (Unitika (N0350WT0) | 35 | 0.2 | 0.084 | — | 0.484 |
| B | 2 | Polyester/polypropylene (Unisel) | 15 | 0.1 | 0.104 | — | — |
| C | 3 | Polyester/polypropylene (Unisel) | 15 | 0.1 | 0.06 | 0.344 | — |
| D | 5 | Polyester (Asahi Chem. Ind.) | 150 | 1.5 | 0.02 | — | 0.412 |
| E | 6 | Rayon (Kuraray) | 100 | 0.8 | 0.072 | 0.248 | — |
| F | 7 | Polyester (Asahi Chem. Ind.) | 50 | 0.5 | 0.104 | — | — |
| G | 8 | Polyester (Asahi Chem. Ind.) | 50 | 0.5 | 0.104 | — | — |

TABLE 4

| Test No. | Sample form | Sample No. | *Staphylococcus aureus* | | | *Pseudomonas aeruginosa* | | |
|---|---|---|---|---|---|---|---|---|
| | | | Initial | After 10 days | After 30 days | Initial | After 10 days | After 30 days |
| 1 | Sheet | A | $2 \times 10^4$ | 0 | 0 | $1 \times 10^4$ | 0 | 0 |
| 2 | " | B | $5 \times 10^4$ | 0 | 0 | $3 \times 10^4$ | 0 | 0 |
| 3 | " | C | $5 \times 10^4$ | 0 | 0 | $3 \times 10^4$ | 0 | 0 |
| 4 | " | D | $2 \times 10^4$ | 0 | 0 | $1 \times 10^4$ | 0 | 0 |
| 5 | " | E | $5 \times 10^4$ | 0 | 0 | $3 \times 10^4$ | 0 | 0 |
| 6 | " | F | $5 \times 10^4$ | 0 | 0 | $3 \times 10^4$ | 0 | 0 |
| 7 | " | G | $2 \times 10^4$ | 0 | 0 | $1 \times 10^4$ | 0 | 0 |
| 8 | Powder | 1 | $2 \times 10^4$ | 0 | $3 \times 10^4$ | $1 \times 10^4$ | $2 \times 10$ | $6 \times 10^2$ |
| 9 | " | 5 | $2 \times 10^4$ | 0 | $3 \times 10^4$ | $1 \times 10^4$ | $5 \times 10^2$ | $8 \times 10^3$ |

TABLE 4-continued

| Test No. | Sample form | Sample No. | Staphylococcus aureus | | | Pseudomonas aeruginosa | | |
|---|---|---|---|---|---|---|---|---|
| | | | Initial | After 10 days | After 30 days | Initial | After 10 days | After 30 days |
| 10 | Control | — | $2 \times 10^4$ | $3 \times 10^8$ | above $10^{10}$ | $1 \times 10^4$ | $5 \times 10^4$ | $3 \times 10^5$ |

TABLE 5

| Test No. | Antibacterial agent | Specific surface area $(m^2/g)$ | Sample form | Silver oozing (PPb) |
|---|---|---|---|---|
| 1 | Antibacterial alumino-silicate No. 1 | 720 | Sheet (No. A) | 19 |
| 2 | Antibacterial alumino-silicate No. 2 | 720 | Sheet (No. B) | 23 |
| 3 | Antibacterial alumino-silicate No. 3 | 930 | Sheet (No. C) | 15 |
| 4 | Antibacterial alumino-silicate No. 5 | 860 | Sheet (No. D) | 6 |
| 5 | Antibacterial alumino-silicate No. 6 | 860 | Sheet (No. E) | 10 |
| 6 | Antibacterial alumino-silicate No. 7 | 860 | Sheet (No. F) | 9 |
| 7 | Antibacterial alumino-silicate No. 8 | 580 | Sheet (No. G) | 51 |
| 8 | Antibacterial alumino-silicate No. 2 | 720 | Powder | 2100 |
| 9 | Antibacterial alumino-silicate No. 7 | 860 | " | 2600 |
| 10 | Antibacterial alumino-silicate No. 8 | 580 | " | 1700 |
| 11 | Silver-spreaded active carbon | 1080 | Granules | 5200 |

Figure 4:
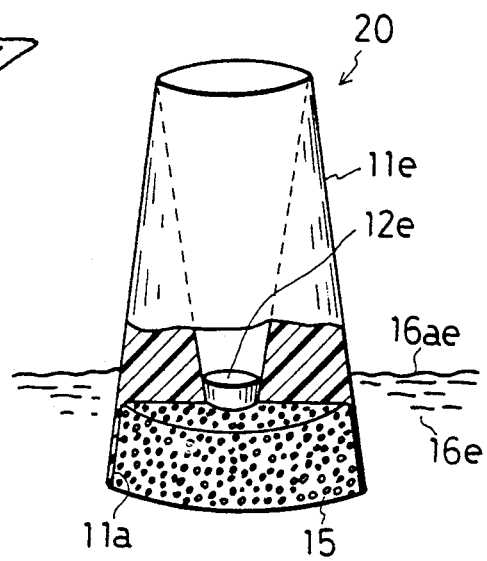
FIGS. 3, 4 and 5 show each an example of the application of the same.
Figure 5:
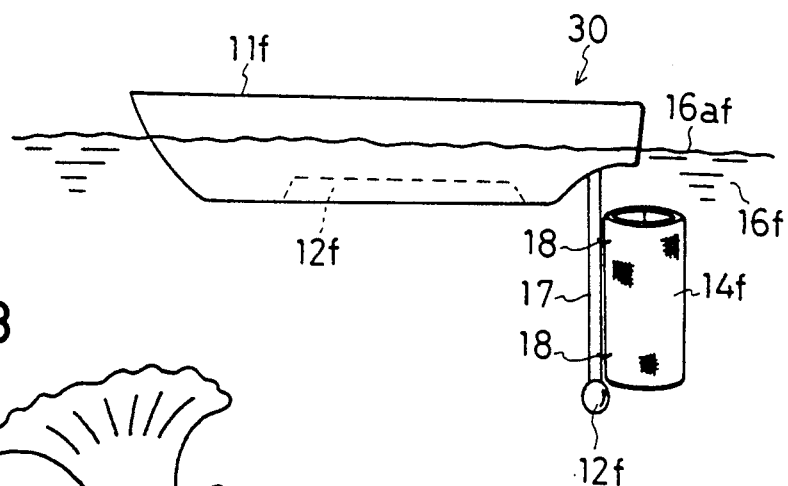
Figure 3:
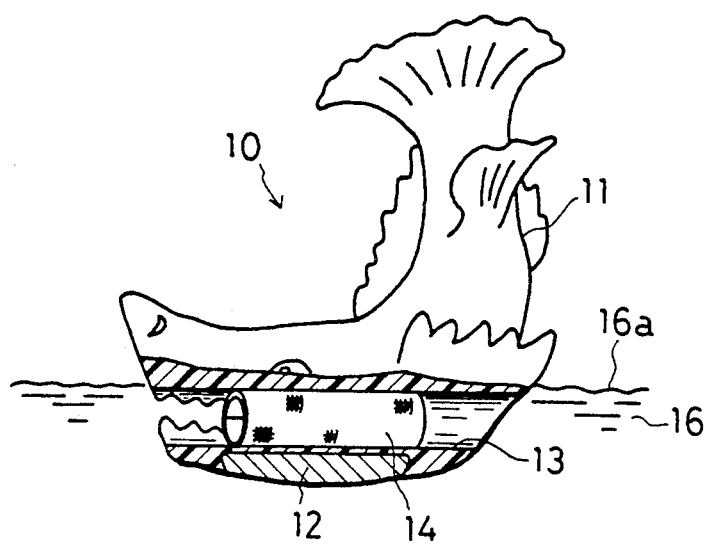

FIGS. 3 to 5 show each an antibacterial product for water comprising the abovementioned antibacterial material for water, wherein said antibacterial material is bound to a material floating in water in such a manner that said floating material is afloat in water while said antibacterial material is placed in the water.

Now an antibacterial product 10 for water shown in FIG. 3 will be described in detail. The floating material 11 may be, for example, a molded plastic product. This floating material 11 may be in various forms, for example, a solid, a hollowing product or a foaming product, so long as it can float in water.

A weight 12 is provided in the bottom of the floating material 11. Thus some portion of the floating material 11 is submerged under water 16 while the residual portion of the same keeps afloat on the water surface 16a. The submerged portion of the floating material 11 is provided with a through hole 13. Both ends of the through hole 13 are opened to thereby allow water to pass therethrough. The through hole 13 is provided with an antibacterial material 14 for water therein which is obtained by molding the same antibacterial material for water as the one shown in FIG. 1 into a cylindrical form.

When the floating material 11 of this antibacterial product 10 for water is afloat in water 16, the antibacterial material 14 is located in the water. In this state, the water 16 passes through the through hole 13 and then sterilized with the antibacterial material 14 therein. Thus the propagation of microorganisms such as bacteria and fungi living in the water can be inhibited. Further the growth of algae can be inhibited thereby. In the above state, the floating material 11 would move as the water 16 moves. The floating material 11 would be also moved by a wind, if the wind blows toward that portion of the material 11 which is above the water surface 16a. As a result, the antibacterial material 14 would also move therewith and thus the antibacterial product can exert said antibiotic effect over a wide range of the water 16.

Next an antibacterial product 20 for water shown in FIG. 4 will be described. A foaming molded product coated with a fabric is used as an antibacterial material 15 for water. This antibacterial material is placed in a cavity 11a at the bottom of the floating material 11a. The foaming molded product may be prepared by mixing a carrier containing the abovementioned antibacterial agent with a plastic or ceramic material and then molding the obtained mixture into a foaming product.

In FIG. 4, parts which seem to correspond to those described in the above FIG. 3 are shown by the same numerals as those in FIG. 3 accompanied by "e" in order to avoid any duplicated description. The same applies to FIG. 5 wherein "f" is added to each corresponding numeral.

The antibacterial product 30 for water shown in FIG. 5 comprises a floating material 11f provided with a supporting rod 17 to which an antibacterial material 14f for water similar to the one used in FIG. 2 is bound with hooks 18.

We claim:

1. An antibacterial material for water which comprises a carrier containing an antibacterial agent and a fabric surrounding said carrier reducing oozing of said antibacterial agent, and keeping the surface of said agent free from dead microbial cells, said fabric having a basis weight from 10 to 180 g/m² which provides voids among a number of fibers to permit water and microorganisms contained therein to pass while preventing contaminants from passing therethrough.

2. An antibacterial material for water as set forth in claim 1, wherein said fabric is a nonwoven fabric having a basis weight of 15 to 150 g/m².

3. An antibacterial material for water as set forth in claim 2, wherein said nonwoven fabric comprises one or more resins selected from the group consisting of polyester, polypropylene and polyamide resins and rayon.

4. An antibacterial material for water as set forth in claim 1, wherein said carrier is a porous material having a specific surface area of 500 m²/g or above.

* * * * *